United States Patent [19]

Tagawa et al.

[11] Patent Number: 5,093,019
[45] Date of Patent: Mar. 3, 1992

[54] LIQUID SEPARATING AGENT CONSISTING ESSENTIALLY OF A COPOLYMER OF AN α-OLEFIN AND A MALEIC

[75] Inventors: Toru Tagawa, Yokohama; Hideki Yamanouchi, Machida; Youichirou Tsuji, Yokohama, all of Japan

[73] Assignee: Mitsubishi Kasei Corporation, Tokyo, Japan

[21] Appl. No.: 444,950

[22] Filed: Dec. 4, 1989

[30] Foreign Application Priority Data

Dec. 8, 1988 [JP] Japan .................. 63-310859

[51] Int. Cl.⁵ .................. B01D 17/00; B01D 21/26; C09K 3/00
[52] U.S. Cl. .................. 252/60; 210/516; 210/789; 526/324
[58] Field of Search .................. 252/60; 210/514, 516, 210/782, 789, 698; 526/324

[56] References Cited

U.S. PATENT DOCUMENTS

| | | | |
|---|---|---|---|
| 4,310,430 | 1/1982 | Ichikawa et al. | 252/60 |
| 4,426,290 | 1/1984 | Ichikawa et al. | 252/60 |
| 4,526,950 | 7/1985 | Grava | 526/324 |
| 4,770,779 | 9/1988 | Ichikawa et al. | 252/60 |
| 4,828,720 | 5/1989 | Kuroda et al. | 210/516 |
| 4,931,197 | 6/1990 | Beck et al. | 526/324 |

FOREIGN PATENT DOCUMENTS

| | | |
|---|---|---|
| 0039898 | 11/1981 | European Pat. Off. . |
| 57-149964 | 9/1982 | Japan . |
| 58-035463 | 3/1983 | Japan . |
| 58-206964 | 12/1983 | Japan . |
| 62-197765 | 9/1987 | Japan . |

*Primary Examiner*—Paul Lieberman
*Assistant Examiner*—Christine A. Skane
*Attorney, Agent, or Firm*—Oblon, Spivak, McClelland, Maier & Neustadt

[57] ABSTRACT

A liquid separating agent consisting essentially of a copolymer of an α-olefin having from 6 to 20 carbon atoms and a maleic acid diester with a copolymer composition (molar ratio) such that the maleic acid diester is more than 1.4 mols relative to 1 mol of the α-olefin, said copolymer having a molecular weight within a range of from 1,000 to 30,000.

13 Claims, No Drawings

LIQUID SEPARATING AGENT CONSISTING ESSENTIALLY OF A COPOLYMER OF AN α-OLEFIN AND A MALEIC

The present invention relates to a liquid separating agent. Particularly, the present invention relates to a liquid separating agent useful for separating components having different specific gravities present in a liquid sample by utilizing the difference of the specific gravities, which has a specific gravity falling in-between the specific gravities of the two components and which is capable of forming a partition wall between the two components to facilitate the separation of the two components. More particularly, the present invention relates to a blood separating agent for separating a blood serum component and a blood clot component, or blood plasma component and a blood cell component, present in blood, by utilizing the difference in their specific gravities, which makes the separation of the two components possible by forming a partition wall between the two components, and which does not substantially absorb a drug contained in the blood serum or in the blood plasma.

Various agents have been known as separating agents useful for such a separation operation. For example, U.S. Pat. No. 4,310,430 discloses an agent which contains a specific α-olefin-maleic acid diester copolymer as the main component and fine inorganic particles such as silica gel or clay as an additive to control the specific gravity or viscosity or to maintain the shape. U.S. Pat. No. 4,828,720 discloses a separating agent which comprises a copolymer of an α-olefin with an α,β-unsaturated dicarboxylic acid diester, or a copolymer of styrene with an α,β-unsaturated dicarboxylic acid diester, as the main component and a certain organic gelling agent added thereto. Further, separating agents containing a silicone oil (Japanese Unexamined Patent Publication No. 2120/1979) and a chlorinated polybutene oil (Japanese Unexamined Patent Publication No. 9718/1982) as the main components, are known.

On the other hand, in recent years, pharmacotherapy has been popular in the clinical practice. Accordingly, it is desired to accurately and promptly measure the drug concentration in blood. With the liquid separating agent as described above, the blood separating treatment can be conducted simply and promptly, and it is accordingly frequently used as a separating agent for blood separation.

However, when conventional commercially available liquid separating agents are employed for liquid separation, there is a problem that due to the influence of the liquid separating agents used, the drug component contained in the blood serum decreases with time. Namely, during the blood separation operation, the drug component to be measured is absorbed by the liquid separating agent, whereby the concentration of the drug in blood decreases with time. Accordingly, it is not advisable to use conventional liquid separating agents for the purpose of measuring the concentration in blood of a certain drug. Therefore, it has been desired to develop a liquid separating agent having such a problem overcome.

Under these circumstances, the present inventors have conducted extensive studies to provide a high performance liquid separating agent free from a decrease with time of the component to be measured, during the separation operation. As a result, they have found it possible to substantially reduce the reduction with time of the component to be measured, by using a liquid separating agent which contains as an essential component a copolymer of an α-olefin with a maleic acid diester with a certain specific compositional ratio. The present invention has been accomplished on the basis of this discovery. Namely, the present invention provides an improvement of a liquid separating agent containing a copolymer of an α-olefin with a maleic acid diester, as the main component.

The present invention provides a liquid separating agent consisting essentially of a copolymer of an α-olefin having from 6 to 20 carbon atoms and a maleic acid diester with a copolymer composition (molar ratio) such that the maleic acid diester is more than 1.4 mols relative to 1 mol of the α-olefin, said copolymer having a molecular weight within a range of from 1,000 to 30,000.

Now, the present invention will be described in detail with reference to the preferred embodiments.

The α-olefin to be used in the present invention has from 6 to 20 carbon atoms and is a linear or low branched hydrocarbon having a carbon-carbon double bond at its terminal. Specifically, an α-olefin obtained by polymerizing ethylene at a low degree is suitably used. However, an α-olefin obtainable by polymerizing propylene or isobutylene at a low degree, may also be employed. In the case of such a low polymerization product, the one having the prescribed carbon number may be obtained by separation such as distillation. In the present invention, α-olefins having from 6 to 20 carbon atoms may be used alone or in combination as a mixture thereof.

If the carbon number of the α-olefin exceeds 20, the resulting copolymer tends to be solid at room temperature, such being undesirable. On the other hand, if the carbon number is smaller than 6, a cumbersome operation such that the reaction has to be conducted under pressure for the preparation of the copolymer, will be required, such being undesirable.

As the maleic acid diester, the one represented by the following formula (1) may be used preferably:

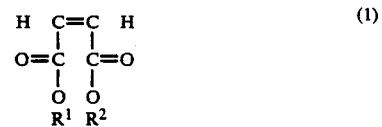

(1)

wherein each of $R^1$ and $R^2$ which may be the same or different is an alkyl group having from 1 to 14 carbon atoms.

The alkyl group for $R^1$ and $R^2$ may be a linear or branched alkyl group having from 1 to 14 carbon atoms such as a methyl group, an ethyl group, a n-propyl group, isopropyl group, a n-butyl group, an isobutyl group, a t-butyl group, a n-hexyl group, a n-octyl group, a n-decyl group or a n-dodecyl group. If the carbon number is larger than 14, the maleic acid diester itself tends to be solid, and the copolymer with the α-olefin will also be solid, such being undesirable. If the carbon number increases, the removal of unreacted maleic acid diester after the copolymerization reaction tends to be difficult. Therefore, the smaller the carbon number, the better. The carbon number is preferably from 1 to 8, and the total carbon number of $R^1$ and $R^2$ is preferably at most 12.

It is required that the liquid separating agent of the present invention contains as an essential component a copolymer having a copolymer composition (molar ratio) such that the maleic acid diester is more than 1.4 mols relative to 1 mol of the α-olefin having from 6 to 20 carbon atoms. If the molar ratio of the maleic acid diester to the α-olefin in the copolymer is not more than 1.4, the amount of the component to be measured during the liquid separation operation, e.g. the drug concentration in blood in the case of the blood separation, substantially decreases with time, such being undesirable. On the other hand, if the molar ratio is too high, the specific gravity of the copolymer will be too high, and it becomes difficult to control the specific gravity by a liquid property regulating agent. The molar ratio is preferably more than 1.4 and not more than 5.1.

In a case where the liquid separating agent of the present invention is employed for blood separation, the molar ratio of the maleic acid diester to the α-olefin in the copolymer is preferably more than 1.4 and not more than 3.0, whereby the change with time of the concentration of an acidic, neutral or basic drug during the separation operation can be suppressed, and the separation can be conducted satisfactorily. Further, with a view to both the suppression of the change with time of the drug concentration and the control of the specific gravity of the copolymer, the molar ratio of the maleic acid diester to the α-olefin, is more preferably within a range of more than 1.4 and not more than 2.5.

The olefin-maleic acid diester copolymer as the essential component of the liquid separating agent of the present invention, can be prepared, for example, by mixing more than 1.4 mols, preferably within a range of more than 1.4 mols and not more than 5.1 mols, of the maleic acid diester to 1 mol of the above-mentioned α-olefin and polymerizing them in accordance with a usual method by heating usually at a temperature of from 100° to 200° C., preferably from 110° to 170° C. in the presence of a peroxide catalyst such as t-butyl peroxyoctoate, di-t-butyl peroxide, t-butyl peroxybenzoate or dicumyl peroxide.

The molecular weight (weight average) of the α-olefin maleic acid diester copolymer thus obtained, is required to be within a range of from 1,000 to 30,000. If the molecular weight is outside this range, the properties as the liquid separating agent, such as flowability, will be inferior. The molecular weight of the α-olefin-maleic acid diester copolymer is preferably from 1,000 to 10,000.

The α-olefin-maleic acid-diester copolymer thus obtained, may be used as it is, as a liquid separating agent. However, various additives may be incorporated for the purpose of adjusting the specific gravity or viscosity depending upon the type of the substance to be separated, or for the purpose of maintaining the shape.

As the liquid property regulating agent to adjust the specific gravity or the viscosity, an α-olefin oligomer, a polybutene oil, an epoxidized soybean oil, an alkyldimethylpolysiloxane, an adipic acid long chain alkyldiester and liquid paraffin may, for example, be mentioned. Among them, the α-olefin oligomer is preferably an α-olefin oligomer having from 6 to 18 carbon atoms and a molecular weight of from 500 to 15,000. The liquid property regulating agent is usually incorporated in an amount of from 0 to 60 parts by weight relative to 100 parts by weight of the α-olefin-maleic acid diester copolymer.

The gelling agent to maintain the liquid separating agent of the present invention in a stabilized non-flowable state before and after the centrifugal separation operation, includes, for example, organic gelling agents such as glutamic acid amide, hardened castor oil and dibenzylidene sorbitol, and inorganic gelling agents such as silica and fatty acid amine derivatives of smectite clay. Such a gelling agent may be incorporated in an amount within a range of from 0.1 to 20 parts by weight relative to 100 parts by weight of the α-olefin-maleic acid diester copolymer. It is preferred to use as the gelling agent an organic gelling agent, since the liquid separating agent thereby forms a uniform system, whereby there will be no problem of phase separation of the liquid separating agent during the heat treatment or during the storage for a long period of time, or under the conditions for centrifugal separation operation. When an organic gelling agent is used as the gelling agent, it is preferably employed in an amount within a range of from 0.1 to 1 part by weight relative to 100 parts by weight of the α-olefin-maleic acid diester copolymer. As the gelling agent, a condensed product of sorbitol with an aromatic aldehyde, is particularly preferred.

The liquid separating agent of the present invention thus prepared, is slightly yellow, transparent and odorless and inactive particularly to blood. Namely it is free from an undesirable phenomenon such as adsorption or elution of blood, shows little absorption of a drug as a component in the blood to be measured and is stable as time passes. Further, it undergoes no physical or chemical change even when subjected to sterilization by radiation of e.g. γ-rays. Accordingly, the liquid separating agent of the present invention is suitable particularly as a blood separating agent.

When the liquid separating agent of the present invention is used for blood separation, it is preferred that the specific gravity (at 25° C.) is within a range of from about 1.02 to 1.08 so that it has a specific gravity intermediate between the blood serum and other components, whereby it is effective for their separation, and yet preferred flowability is attainable for the centrifugal separation operation, and a stabilized state can be maintained for a relatively long period of time before and after the separation operation.

Now, the present invention will be described in further detail with reference to Examples. However, it should be understood that the present invention is by no means restricted by such specific Examples.

EXAMPLE 1

Into a four-necked flask, 56.0 g (0.33 mol) of dodecene (Dialene 12, tradename, manufactured by Mitsubishi Kasei Corporation) and 69.6 g (0.48 mol) of dimethyl maleate were charged. While heating the mixture at about 160° C. under stirring in a nitrogen atmosphere 11 g (0.08 mol) of d-t-butyl peroxide (Kayabutyl D, tradename, manufactured by Kayaku Nury Co.) was added thereto over a period of about 4 hours. Thereafter, the mixture was stirred at about 165° C. for 1 hour, and then heated under reduced pressure to remove low boiling point components.

The amount of a copolymer thereby obtained, was 125 g (yield: 99%). The specific gravity was 1.05, and the molecular weight was about 4,400 as measured by gel permeation chromatography and calculated as polystyrene. The copolymer composition (molar ratio) was α-olefin/maleic acid diester = 1/1.45, as calculated from the values obtained by the elemental analysis of the copolymer obtained.

EXAMPLE 2

Into a four-necked flask, 168 g (1 mol) of dodecene and 216 g (1.5 mol) of dimethyl maleate were charged, and 11 g (0.08 mol) of di-t-butyl peroxide was added thereto under the same condition as in Example 1. Thereafter, the mixture was stirred at about 165° C. for 1 hour and then heated under reduced pressure to remove low boiling point components.

The amount of the copolymer thereby obtained was 379 g (yield: 99%). The specific gravity was 1.05 and the molecular weight was about 3,500 as measured by gel permeation chromatography and calculated as polystyrene. The copolymer composition (molar ratio) was α-olefin/maleic acid diester = 1/1.51.

EXAMPLE 3

Into a four-necked flask, 168 g (1 mol) of dodecene and 288 g (2 mols) of dimethyl maleate were charged, and 20.0 g (0.14 mol) of di-t-butyl peroxide was added thereto under the same condition as in Example 1. Thereafter, the mixture was stirred at about 165° C. for 1 hour and then heated under reduced pressure to remove low boiling point components.

The amount of the copolymer thereby obtained was 448 g (yield: 98%). The specific gravity was 1.08, and the molecular weight was about 3,500. The copolymer composition (molar ratio) was α-olefin/maleic acid diester = 1/2.04.

To 80 g of this copolymer, 20 g of an oligomer (molecular weight: about 3,000) of α-olefin (Dialene 124, tradename, manufactured by Mitsubishi Kasei Corporation) was added to adjust the specific gravity to about 1.03.

EXAMPLE 4

Into a four-necked flask, 42 g (0.25 mol) of dodecene and 180 g (1.25 mols) of dimethyl maleate were charged, and 22 g (0.15 mol) of di-t-butyl peroxide was added thereto over a period of about 8 hours under the same condition as in Example 1. Then, the mixture was stirred at about 165° C. for 1 hour, and then heated under reduced pressure to remove low boiling point components.

The amount of the copolymer thereby obtained was 217 g (yield: 98%). The specific gravity was 1.15, and the molecular weight was about 4,500. The copolymer composition (molar ratio) was α-olefin/maleic acid diester = 1/5.10.

To 70 g of this copolymer, 30 g of an oligomer (molecular weight: about 3,000) of α-olefin (Dialene 124, tradename, manufactured by Mitsubishi Kasei Corporation) was added to adjust the specific gravity to 1.07.

EXAMPLE 5

To 100 g of the mixture of the copolymer and the α-olefin oligomer obtained in Example 3, 0.25 g of dibenzylidene sorbitol was added, and the mixture was heated and stirred at 140° C. for 1 hour. Then, it was left to cool for gellation. The gelled copolymer had a specific gravity of 1.03 and a molecular weight of about 3,500.

EXAMPLE 6

To 100 g of the mixture of the copolymer and the α-olefin oligomer obtained in Example 3, 2.5 g of Benton 30 (a quaternary ammonium salt of smectite clay, manufactured by NL Industry Co.) was added, and the mixture was kneaded by a triple roll for gellation. The gelled copolymer had a specific gravity of 1.04 and a molecular weight of about 3,500.

EXAMPLE 7

Into a four-necked flask, 122 g (1 mol) of octane, 144 g (1 mol) of dimethyl maleate and 244 g (1 mol) of methyl octyl maleate were charged. While heating the mixture at 110° C. under stirring in a nitrogen atmosphere, 21.6 g (0.1 mol) of t-butyl peroxy octoate was added over a period of about 4 hours. Thereafter, the mixture was stirred at about 115° C. for 1 hour and heated under reduced pressure to remove low boiling point components.

The amount of the copolymer thereby obtained was 503 g (yield: 99%). The specific gravity was 1.03, and the molecular weight was about 4,000. The copolymer composition (molar ratio) was α-olefin/maleic acid diester = 1/2.02.

COMPARATIVE EXAMPLE 1

Into a four-necked flask, 168 g (1 mol) of dodecene and 130 g (0.9 mol) of dimethyl maleate were charged. While heating the mixture at 160° C. under stirring in a nitrogen atmosphere, 7.3 g (0.05 mol) of di-t-butyl peroxide was added thereto over a period of about 4 hours. Thereafter, the mixture was stirred at about 165° C. for 1 hour and then heated under reduced pressure to remove low boiling point components.

The amount of the copolymer thereby obtained was 295 g (yield: 99%). The specific gravity was 1.02, and the molecular weight was about 4,000. The copolymer composition (molar ratio) was α-olefin/maleic acid diester = 1/0.9.

TEST EXAMPLE 1

(Test for Adsorption of a Drug)

The separating agents (a copolymer, a mixture of a copolymer and an α-olefin oligomer, and a gelled product thereof) obtained in Examples 1 to 7 and in Comparative Example 1, were evaluated in accordance with the following method.

About 1.5 g of each separating agent was put into a test tube having a predetermined diameter. Then, 1 cc of bovine serum containing a drug at a predetermined concentration was added thereto. The mixture was left to stand still at 20° C. Upon expiration of 72 hours, only the bovine serum was collected, and the amount of the drug contained therein was measured by an immunofluorescent antibody technique. The proportion of the drug concentration in the bovine serum after being left for 72 hours relative to the drug concentration in the initial bovine serum, was obtained and taken as the drug remaining rate.

The results are shown in Table 1. Further, for the purpose of comparison, similar evaluation was conducted with respect to separating agent A (containing a polyester as the essential component, which was gelled by fine silica particles) presently commercially available as a serum separating agent.

TEST EXAMPLE 2

(Separating Test)

To the bottom of a 20 ml test tube, 2 g of a separating agent as identified in Table 1 was injected. Then, 5 ml of a sucrose solution having a specific gravity of 1.08 was slowly injected, and then 5 ml of a colored sucrose solution having a specific gravity of 1.02 was injected in a similar manner to form two liquid layers separated from each other.

This test tube was subjected to centrifugal separation at 3,000 rpm for 20 minutes, whereupon it was confirmed that the separating agent transferred to the intermediate position between the two liquid layers.

The results are shown in Table 1.

TABLE 1

| Separating agents | Drug remaining rate*1 | | | Separating test*2 |
| --- | --- | --- | --- | --- |
| | To acidic drug (Phenobarbital) | To neutral drug (Phenytoin) | To basic drug (Lidocaine) | |
| Example 1 | A | A | C | ○ |
| Example 2 | A | A | B | ○ |
| Example 3 | A | A | A | ○ |
| Example 4 | A | A | A | — |
| Example 5 | A | A | A | — |
| Example 6 | A | A | A | — |
| Example 7 | A | A | A | ○ |
| Comparative Example 1 | A | D | D | ○ |
| Separating agents A | D | D | D | ○ |

*1 A: Drug remaining rate of at least 85%
B: Drug remaining rate of at least 75% and less than 85%
C: Drug remaining rate of at least 70% and less than 75%
D: Drug remaining rate of less than 70%
*2 ○: Transferred to the intermediate position between the two liquid phases.
—: Not tested.

We claim:

1. A blood separating agent consisting essentially of a copolymer of an α-olefin having from 6 to 20 carbon atoms and maleic acid diester represented by the following formula (1):

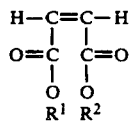

wherein each of $R^1$ and $R^2$ which may be the same or different is an alkyl group having from 1 to 14 carbon atoms, with a copolymer composition (molar ratio) such that the maleic acid diester is more than 1.4 mols and not more than 5.1 mols relative to 1 mol of the α-olefin, said copolymer having a molecular weight within a range of from 1,000 to 30,000.

2. The liquid separating agent according to claim 1, wherein the copolymer composition (molar ratio) is such that the maleic acid diester is more than 1.4 mols and not more than 3.0 mols relative to 1 mol of the α-olefin.

3. The liquid separating agent according to claim 1, wherein the copolymer composition (molar ratio) is such that the maleic acid diester is more than 1.4 mols and not more than 2.5 mols relative to 1 mol of the α-olefin.

4. The liquid separating agent according to claim 1, wherein the maleic acid diester is represented by the following formula (1'):

wherein each of $R^{1'}$ and $R^{2'}$ which may be the same or different is an alkyl group having from 1 to 8 carbon atoms.

5. The liquid separating agent according to claim 1, wherein the maleic acid diester is maleic acid dimethyl ester.

6. The liquid separating agent according to claim 1, which has a specific gravity (at 25° C.) of from 1.02 to 1.08.

7. The liquid separating agent according to claim 1, wherein the copolymer has a molecular weight of from 1,000 to 10,000.

8. The liquid separating agent according to claim 1, which further contains at least one organic gelling agent selected from the group consisting of glutamic acid amide, hardened castor oil and condensed products of sorbitol with an organic aldehyde and/or at least one inorganic gelling agent selected from the group consisting of silica and fatty acid amine derivatives of smectite clay.

9. The liquid separating agent according to claim 8, which contains from 0.1 to 20 parts by weight of an organic and/or inorganic gelling agent relative to 100 parts by weight of the copolymer.

10. The liquid separating agent according to claim 8, which contains from 0.1 to 1 part by weight of an organic gelling agent relative to 100 parts by weight of the copolymer.

11. The liquid separating agent according to claim 10, wherein the organic gelling agent is a condensation product of sorbitol with an aromatic aldehyde.

12. The liquid separating agent according to claim 1, which further contains a liquid property regulating agent, wherein said liquid property regulating agent is at least one member selected from the group consisting of an α-olefin oligomer, a polybutene oil, an epoxidized soybean oil, an alkyldimethylpolysiloxane, an adipic acid long chain alkyldiester and liquid paraffin.

13. The liquid separating agent according to claim 12, wherein the liquid property regulating agent is in an amount of from 0 to 60 parts by weight relative to 100 parts by weight of the copolymer.

* * * * *

UNITED STATES PATENT AND TRADEMARK OFFICE
CERTIFICATE OF CORRECTION

PATENT NO. : 5,093,019
DATED : March 3, 1992
INVENTOR(S) : Toru Tagawa et al.

It is certified that error appears in the above-identified patent and that said Letters Patent is hereby corrected as shown below:

On the title page, item (54) should read --LIQUID SEPARATING AGENT CONSISTING ESSENTIALLY OF A COPOLYMER OF AN ALPHA-OLEFIN ACID DIESTER--.

Signed and Sealed this

Sixth Day of July, 1993

Attest:

MICHAEL K. KIRK

*Attesting Officer*      *Acting Commissioner of Patents and Trademarks*